US012624401B2

(12) United States Patent　　　　(10) Patent No.: US 12,624,401 B2
Rizik et al.　　　　　　　　　　　　(45) Date of Patent:　　May 12, 2026

(54) SINGLE INPUT MULTIPLEX DECISION SYSTEMS AND METHODS OF USING THE SAME

(71) Applicant: TECHNION RESEARCH & DEVELOPMENT FOUNDATION LIMITED, Haifa (IL)

(72) Inventors: Luna Rizik, Haifa (IL); Ramez Daniel, Haifa (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 1109 days.

(21) Appl. No.: 17/614,534

(22) PCT Filed: May 28, 2020

(86) PCT No.: PCT/IL2020/050601
§ 371 (c)(1),
(2) Date: Nov. 28, 2021

(87) PCT Pub. No.: WO2020/240568
PCT Pub. Date: Dec. 3, 2020

(65) Prior Publication Data
US 2022/0228228 A1　　Jul. 21, 2022

Related U.S. Application Data

(60) Provisional application No. 62/872,800, filed on Jul. 11, 2019, provisional application No. 62/853,285, filed on May 28, 2019.

(51) Int. Cl.
*C12Q 1/6897*　　(2018.01)
*C12N 15/113*　　(2010.01)
(Continued)

(52) U.S. Cl.
CPC .......... *C12Q 1/6897* (2013.01); *C12N 15/113* (2013.01); *C12N 15/70* (2013.01);
(Continued)

(58) Field of Classification Search
CPC .............. C12Q 1/6897; C12N 2800/40; C12N 2830/001; C12N 15/635; G06N 3/002; G06N 3/123
See application file for complete search history.

(56) References Cited

U.S. PATENT DOCUMENTS

| | | |
|---|---|---|
| 6,342,596 B1 | 1/2002 | Voellmy |
| 6,737,269 B2 | 5/2004 | Gardner |
| 2017/0145426 A1 | 5/2017 | Xie |

FOREIGN PATENT DOCUMENTS

WO　　WO-2013155439 A1 * 10/2013　............. B82Y 10/00

OTHER PUBLICATIONS

Lin, Shudai, et al. "Characteristics of Antisense Transcript Promoters and the Regulation of Their Activity." International Journal of Molecular Sciences, vol. 17, No. 1, Dec. 23, 2015, pp. 9-9, https://doi.org/10.3390/ijms17010009. Accessed Mar. 13, 2024. (Year: 2015).*

(Continued)

*Primary Examiner* — Kimberly Chong
*Assistant Examiner* — Africa M Mcleod
(74) *Attorney, Agent, or Firm* — The Roy Gross Law Firm, LLC; Roy D. Gross

(57)　　　ABSTRACT

The present invention is directed to a single input multiplex decision expression system, and a method of using same, such as for expressing a reporter protein.

20 Claims, 2 Drawing Sheets

(51) Int. Cl.
| | |
|---|---|
| *C12N 15/63* | (2006.01) |
| *C12N 15/70* | (2006.01) |
| *G06N 3/00* | (2023.01) |
| *G06N 3/123* | (2023.01) |

(52) U.S. Cl.
CPC ........ *C12N 15/635* (2013.01); *C12N 2310/12* (2013.01); *C12N 2800/101* (2013.01); *C12N 2800/40* (2013.01); *C12N 2830/001* (2013.01); *G06N 3/002* (2013.01); *G06N 3/123* (2013.01)

(56) References Cited

OTHER PUBLICATIONS

O'Hanlon Cohrt, Karen. "How to Manipulate Plasmid Copy Number." Bitesize Bio, Jan. 14, 2015, web.archive.org/web/20150410081023/bitesizebio.com/22824/how-to-manipulate-plasmid-copy-number/#expand. Accessed Sep. 23, 2025. (Year: 2015).*

Wild, Jadwiga, et al. "Conditionally Amplifiable BACs: Switching from Single-Copy to High-Copy Vectors and Genomic Clones." Genome Research, vol. 12, No. 9, Sep. 1, 2002, pp. 1434-1444, https://doi.org/10.1101/gr.130502. (Year: 2002).*

International search report for PCT/IL2020/050601 dated Sep. 17, 2020.

Written opinion for PCT/IL2020/050601 dated Sep. 17, 2020.

Daniel, Ramiz, Jacob R. Rubens, Rahul Sarpeshkar, and Timothy K. Lu. "Synthetic analog computation in living cells." Nature 497, No. 7451 (2013): 619-623.

* cited by examiner

SINGLE INPUT MULTIPLEX DECISION SYSTEMS AND METHODS OF USING THE SAME

CROSS-REFERENCE TO RELATED APPLICATIONS

This application is a National Phase of PCT Patent Application No. PCT/IL2020/050601 having International filing date of May 28, 2020, which claims the benefit of priority of U.S. Provisional Patent Application No. 62/853,285 titled "SINGLE INPUT MULTIPLEX DECISION SYSTEMS AND METHODS OF USING THE SAME", filed May 28, 2019, and of U.S. Provisional Patent Application No. 62/872,800 titled "SINGLE INPUT MULTIPLEX DECISION SYSTEMS AND METHODS OF USING THE SAME", filed Jul. 11, 2019, the contents of which are incorporated herein by reference in their entirety.

FIELD OF INVENTION

The present invention, in some embodiments, thereof, is in the field of molecular biology and genetic engineering.

BACKGROUND

Many applications of genetic or metabolic engineering require inducible expression of the desired pathway. Inducible promoters are one of the easiest and most effective ways to control gene expression. However, in more sophisticated applications there is a need to coordinate expression of multiple genes. The acceptable/common solution utilizes different inducible promoters for different genes. The downside of this approach is that it requires multiple inducers which can be expensive and/or hard to obtain/produce. Moreover, the use of different inducers may cause crosstalk and/or cell toxicity.

SUMMARY

The present invention, in some embodiments thereof, is directed to a single input multiplex decision expression system, and methods of use thereof, such as for expressing a reporter protein.

According to a first aspect, there is provided a system comprising: (a) a first expression vector comprising a first promoter sequence operably linked to a sequence encoding a first regulatory protein, wherein the first promoter is responsive to an input signal, and further comprising a second promoter sequence operably linked to a sequence encoding a second regulatory protein, wherein the second promoter is responsive to the first regulatory protein; (b) a second expression vector comprising a third promoter operably linked to a sequence encoding a third regulatory protein; and (c) a third expression vector comprising a fourth promoter sequence operably linked to a sequence encoding an output protein, wherein the fourth promoter is responsive to the second regulatory protein, and further comprising a fifth promoter sequence located between the fourth promoter and the sequence encoding the output protein, wherein the fifth promoter is responsive to the first regulatory protein and to the third regulatory protein, and wherein the fifth promoter sequence transcribes in a direction opposite to the fourth promoter sequence.

According to another aspect, there is provided a system comprising: (a) a first expression vector comprising a first promoter sequence operably linked to a sequence encoding a first regulatory protein, wherein the first promoter is responsive to an input signal, and further comprising a second promoter sequence operably linked to a sequence encoding a second regulatory protein, wherein the second promoter is responsive to the first regulatory protein; (b) a second expression vector comprising a third promoter sequence operably linked to a sequence encoding a first output protein, wherein the third promoter is responsive to the second regulatory protein and wherein the sequence encoding the first output protein further comprises a degradation tag, and further comprising a fourth promoter sequence located between the third promoter and the sequence encoding the first output protein, wherein the fourth promoter sequence transcribes in a direction opposite to the third promoter sequence, and further comprising a fifth promoter sequence operably linked to a sequence encoding the first output protein, wherein the fifth promoter is responsive to the first regulatory protein; and (c) a third expression vector comprising the fourth promoter operably linked to a sequence encoding a second output protein.

According to another aspect, there is provided a cell or a cell lysate comprising the system of the invention.

According to another aspect, there is provided a composition comprising the cell or cell lysate of the invention.

According to another aspect, there is provided a method for expressing one or more output proteins using a single input signal, the method comprising: (a) providing a cell or a cell lysate comprising the system of the invention; (b) contacting the cell or the cell lysate with an input signal capable of activating the system; and (c) detecting the expression of the one or more output proteins in the cell or the cell lysate.

According to another aspect, there is provided a method for converting an analog signal to a digital output in a cell, the method comprising contacting the cell with the system of the invention, thereby converting an analog signal to a digital output in the cell.

In some embodiments, one of: (i) the first promoter is responsive to the first regulatory protein; (ii) the second regulatory protein is expressed upon activation of the second promoter; (iii) the third regulatory protein is expressed upon activation of the third promoter; (iv) the output protein is expressed upon activation the fourth promoter is activated; (v) the expression of the output protein is reduced upon activation of the fifth promoter; and any combination of (i)-(v).

In some embodiments, when the fifth promoter is repressed, the expression of the output protein is activated.

In some embodiments, (i) the first expression vector is a low copy plasmid, (ii) the second expression vector is a medium copy plasmid, (iii) the third expression vector is a high copy plasmid; and any combination of (i)-(iii).

In some embodiments, the second expression vector further comprises a first regulatory sequence, and wherein the third expression vector further comprises a second regulatory sequence.

In some embodiments, the first regulatory sequence is located between the third promoter and the sequence encoding the third regulatory protein.

In some embodiments, the first regulatory sequence regulates translation of the third regulatory protein.

In some embodiments, the first regulatory sequence comprises a ribosomal binding site.

In some embodiments, the second regulatory sequence is located between the fourth promoter and the sequence encoding the output protein.

In some embodiments, the second regulatory sequence is located between the fifth promoter and the sequence encoding the output protein.

In some embodiments, the second regulatory sequence is a non-coding polynucleotide.

In some embodiments, the non-coding polynucleotide is a catalytic polynucleotide.

In some embodiments, the catalytic polynucleotide is a ribozyme.

In some embodiments, the sequence encoding the third regulatory protein further comprises a degradation tag.

In some embodiments, the first promoter sequence and the sequence encoding a first regulatory protein, and the second promoter sequence and the sequence encoding a second regulatory protein, are located on separate expression vectors.

In some embodiments, (i) the first promoter is responsive to the first regulatory protein; (ii) the second regulatory protein is expressed upon activation of the second promoter; (iii) the first output protein of the second expression vector is expressed, upon activation of the fifth promoter.

In some embodiments, the first regulatory protein binds to the fourth promoter with greater affinity than the first regulatory protein binds to the first promoter or the second promoter.

In some embodiments, when the fourth promoter is activated the second output protein is expressed, expression of the first output protein comprising a degradation tag from the second expression vector is repressed, or any combination thereof.

In some embodiments, when the third promoter is activated the first output protein comprising a degradation tag of the second expression vector is expressed.

In some embodiments, (i) the first expression vector is a low copy plasmid; (ii) the second expression vector is a high copy plasmid; and (iii) the third expression vector is a medium copy plasmid; and any combination of (i)-(iii).

In some embodiments, the second expression vector further comprises a first regulatory sequence, and the third expression vector further comprises a second regulatory sequence.

In some embodiments, the first regulatory sequence is located between the third promoter and the sequence encoding the first output protein comprising a degradation tag of the second expression vector, an wherein the second regulatory sequence is located between the fourth promoter and the sequence encoding the second output protein of the third expression vector.

In some embodiments, the first regulatory sequence is located between the fourth promoter and the sequence encoding the first output protein comprising a degradation tag of the second expression vector.

In some embodiments, any one of the first and the second regulatory sequences is a non-coding polynucleotide.

In some embodiments, the third promoter sequence and the sequence encoding a first output protein comprising a degradation tag and the fourth promoter sequence, and the fifth promoter sequence and the sequence encoding the first output protein, are located on separate expression vectors.

In some embodiments, the first promoter and the second promoter are mutated variant promoters of the fourth promoter.

In some embodiments, the first regulatory protein binds to the mutated variant promoters with reduced binding affinity compared to the binding affinity of the first regulatory protein to the fourth promoter.

In some embodiments, the first promoter is activated when bound to the input signal.

In some embodiments, when the first promoter is activated the first regulatory protein is expressed.

In some embodiments, the second promoter, the fourth promoter, and the fifth promoter are activated when bound to the first regulatory protein.

In some embodiments, the third promoter is activated when bound to the second regulatory protein.

In some embodiments, the cell is a bacterial cell.

In some embodiments, the cell or cell lysate further comprises an input signal.

In some embodiments, contacting comprises contacting the cell or the cell lysate with different concentrations of the input signal.

In some embodiments, the method further comprises a step of determining the expression levels of the one or more output proteins.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION

Figure 1A:
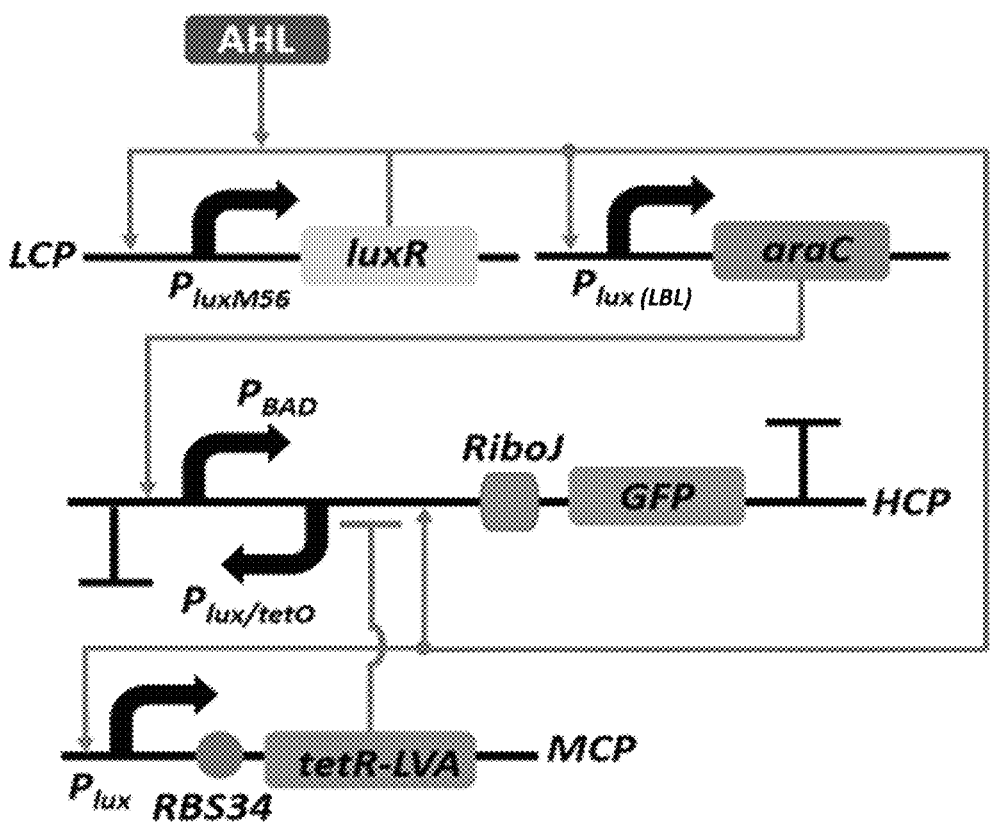
FIGS. 1A-1B include a non-limiting scheme of a three single input multiplex decision (SMID) system, and a graph showing how a single inducer or input signal (e.g., N-Acyl homoserine lactone; AHL) can be converted to three-logic states. A three states SIMD is implemented in $E.$ $coli$ bacteria cells using three transcription factors (i.e., regulatory proteins). (1A) The three states SIMD comprises a mutated promoter, i.e., $P_{luxM56}$, providing a positive feedback loop, which regulates LuxR expression. The LuxR protein activates expression of the Arabinose C protein (via a low basal level Lux promoter ($P_{lux\ (LBL)}$, which in turn activates the $P_{BAD}$ promoter to expresses the green fluorescent protein (GFP; (i.e., an output protein). The $P_{BAD}$ promoter is negatively regulated by a fused antisense combinational promoter comprising $P_{lux/tetO}$. A reverse complementary terminator is cloned upstream to $P_{BAD}$ to perturb the activity of an antisense RNA polymerase. A RiboJ (i.e., regulatory RNA sequence) is used to cleave the 5'-untranslated region (UTR) of the GFP mRNA. The expression of Tetracycline repressor (tetR) is regulated by the Plux promoter and is therefore activated by the LuxR protein. The tuning of the ribosome-binding sequence of Plux (RBS34), regulates tetR and converts the AHL signal to three-logic states (low/medium/high). A small stable RNA A (ssRA) degradation tag (LVA) was added to TetR. (1B) is a graph showing that the three states SMID system expresses GFP is an inducer concentration dependent manner (i.e., "low", "medium", and "high"). Low copy plasmid (LCP); Medium copy plasmid (MCP); and High copy plasmid (HCP).

The present invention, in some embodiments thereof, is directed to a 3 single input multiplex decision (SMID) system. As used herein, the term "3 SMID system" refers to a system comprising: (a) a first expression vector comprising a first promoter sequence operably linked to a sequence encoding a first regulatory protein, wherein the first promoter is responsive to an input signal, and further comprising a second promoter sequence operably linked to a sequence encoding a second regulatory protein, wherein the second promoter is responsive to the first regulatory protein; (b) a second expression vector comprising a third promoter operably linked to a sequence encoding a third regulatory protein; and (c) a third expression vector comprising a fourth promoter sequence operably linked to a sequence encoding an output protein, wherein the fourth promoter is responsive to the second regulatory protein, and further comprising a fifth promoter sequence located between the fourth promoter and the sequence encoding the output protein, wherein the fifth promoter is responsive to the first regulatory protein and to the third regulatory protein, and wherein the fifth promoter sequence transcribes in a direction opposite to the fourth promoter sequence.

The present invention, in some embodiments thereof, is directed to a 4 single input multiplex decision (SMID) system. As used herein, the term "4 SMID system" refers to a system comprising: (a) a first expression vector comprising a first promoter sequence operably linked to a sequence encoding a first regulatory protein, wherein the first promoter is responsive to an input signal, and further comprising a second promoter sequence operably linked to a sequence encoding a second regulatory protein, wherein the second promoter is responsive to the first regulatory protein; (b) a second expression vector comprising a third promoter sequence operably linked to a sequence encoding a first output protein, wherein the third promoter is responsive to the second regulatory protein and wherein the sequence encoding the first output protein further comprises a degradation tag, and further comprising a fourth promoter sequence located between the third promoter and the sequence encoding the first output protein, wherein the fourth promoter sequence transcribes in a direction opposite to the third promoter sequence, and further comprising a fifth promoter sequence operably linked to a sequence encoding the first output protein, wherein the fifth promoter is responsive to the first regulatory protein; and (c) a third expression vector comprising the fourth promoter operably linked to a sequence encoding a second output protein.

The term "promoter" as used herein refers to a group of transcriptional control modules that are clustered around the initiation site for an RNA polymerase i.e., RNA polymerase II. Promoters are composed of discrete functional modules, each consisting of approximately 7-20 bp of DNA, and containing one or more recognition sites for regulatory proteins, such as a transcriptional activator or repressor.

In some embodiments, the promoter is operably linked to a polynucleotide sequence of interest (i.e., targeted for expression). The term "operably linked" is intended to mean that the polynucleotide sequence of interest is linked to the regulatory element or elements in a manner that allows for expression of the polynucleotide sequence (e.g., in an in vitro transcription/translation system, artificial cell, or in a host cell when the expression vector is introduced into the artificial or host cell).

In some embodiments, a promoter is considered "responsive" to an input signal if the input signal modulates the function of the promoter, indirectly or directly. In some embodiments, an input signal may positively modulate a promoter such that the promoter activates or increases, transcription of a nucleic acid to which it is operably linked. In some embodiments, an input signal may negatively modulate a promoter such that the promoter is prevented from activating or inhibits, or decreases, transcription of a nucleic acid to which it is operably linked. In some embodiments, an input signal modulates the function of the promoter directly by binding to the promoter or by acting on the promoter without an intermediate signal. For a non-limiting example, the LuxR protein as exemplified hereinbelow, modulates the plux promoter by binding to a region of the plux promoter. Thus, the LuxR protein is considered according to this example as an input signal that directly modulates the plux promoter. Contrary, an input signal is considered to modulate the function of a promoter indirectly if the input signal modulates the promoter via an intermediate signal. For example, acyl-homoserine-lactone (AHL) modulates (e.g., activates) the LuxR protein, which, in turn, modulates (e.g., activates) the plux promoter. Thus, AHL is considered according to this example as an input signal that indirectly modulates the plux promoter.

In some embodiments, the first promoter is responsive to the first regulatory protein.

As used herein, the term "input signal" refers to any chemical (e.g., small molecule) or non-chemical (e.g., light or heat) signal in a cell, or to which the cell is exposed, that modulates, i.e., activates or inhibits, directly or indirectly, a component (e.g., a promoter) of a SMID system. In some embodiments, an input signal is a biomolecule that modulates the function of a promoter (referred to as direct modulation), or is a signal that modulates a biomolecule, which in turn modulates the function of the promoter (referred to as indirect modulation). In some embodiments, an input signal is endogenous to a cell or a normally exogenous condition, compound, protein, or any combination thereof, that contacts a promoter of a SMID system in such a way as to be active in modulating (e.g., inducing or repressing) transcriptional activity from a promoter responsive to the input signal (e.g., an inducible promoter).

Non-limiting examples of chemical input signals include, but not limited to, signals extrinsic or intrinsic to a cell, such as amino acids and amino acid analogs, saccharides and polysaccharides, nucleic acids, protein transcriptional activators and repressors, cytokines, toxins, petroleum-based compounds, metal containing compounds, salts, ions, enzymes, enzyme substrates, enzyme substrate analogs, hormones, quorum-sensing molecules, and others.

In some embodiments, an input signal is a molecule selected from N-Acyl homoserine lactones (AHL). In some embodiments, the input signal comprises N-(β-keto-caproyl)-L-Homoserine lactone. In some embodiments, the input signal is N-(β-ketocaproyl)-L-Homoserine lactone.

Non-limiting examples of non-chemical input signals include, without limitation, changes in physiological conditions, such as changes in pH, light, temperature, radiation, osmotic pressure, saline gradients, or any combination thereof.

According to the present invention, in some embodiments thereof, a promoter responsive to an input signal and/or regulatory protein is considered an "inducible" promoter. Inducible promoters for use according to the present invention include any inducible promoter described herein or known to one of ordinary skill in the art. Non-limiting examples of inducible promoters include, but are not limited to, chemically-regulated, biochemically-regulated, and/or physically-regulated promoters, such as alcohol-regulated promoters, tetracycline-regulated promoters (e.g., anhydro-tetracycline (aTc)-responsive promoters and/or other tetra-cycline-responsive promoter systems, which include a tet-racycline repressor protein (tetR), a tetracycline operator sequence (tetO), and/or a tetracycline trans-activator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regu-lated promoters (e.g., promoters derived from metallothio-nein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and/or light-regulated promoters (e.g., light responsive promoters from plant cells), or any combi-nation thereof.

As used herein, the term "positive-feedback promoter" refers to a promoter that is operably linked to a nucleic acid encoding a regulatory protein (e.g., transcription factor such as LuxR) that binds to that promoter to "self-regulate" expression of the regulatory protein. In some embodiments, a positive-feedback promoter is operably linked to a nucleic acid encoding a transcription factor that binds to the posi-tive-feedback promoter to regulate its own expression. In some embodiments, a positive-feedback promoter is modi-fied (e.g., mutated) such that the binding affinity of the promoter for a particular regulatory protein, or vice versa, is altered (e.g., reduced), relative to the binding affinity of the unmodified or wild type promoter for that same regulatory protein.

In some embodiments, the promoter is an output pro-moter. As used herein, the term "output promoter" refers to a promoter that is operably linked to a nucleic acid encoding an output molecule. In some embodiments, an output pro-moter is responsive to a regulatory protein, such as, for example, a transcription factor. In some embodiments, an output promoter is modified such that the affinity of the promoter for a particular regulatory protein is altered, rela-tive to the affinity of the unmodified promoter for that same regulatory protein. As used herein, the terms "modified" or "modification" encompass a mutation, a substitution, an insertion/deletion (InDel), an inversion, and the like. As used herein, the term "altered" is equivalent to modulation and encompasses both increase or elevation, and decrease or reduction.

According to the present invention, a promoter may contain a (e.g., at least one) modification, relative to a wild-type (unmodified) version of the same promoter. In some embodiments, the modification alters the affinity of a regulatory protein (e.g., transcription factor) for one pro-moter (e.g., positive-feedback promoter) relative to another promoter (e.g., output promoter) in SMID system of the invention. As exemplified herein, both the positive-feedback promoter and the output promoter are based on the plux promoter, with the former driving expression of LuxR and the latter driving expression of GFP. The relative affinity of each LuxR-responsive promoter for LuxR can be altered, for example, by modifying one or more nucleic acids in the lux box region of the promoter.

Promoter modifications may include, for example, single or multiple nucleotide mutations (e.g., A to T, A to C, A to G, T to A, T to C, T to G, C to A, C to T, C to G, G to A, G to T, or G to C), insertions and/or deletions (relative to an unmodified promoter) in a region, or a putative region, that affects regulatory protein binding to the region. In some embodiments, a modification is in a regulatory protein (e.g., transcription factor) binding site of a promoter. A promoter may contain a single modification or more than one (e.g., 2, 3, 4, 5, 6, 7, 8, 9, 10 or more) modifications to, for example, achieve the desired binding affinity for a cognate regulatory protein. A promoter may contain a single regulatory protein (e.g., transcription factor) binding site or a plurality of regulatory protein (e.g., transcription factor) binding sites. A plurality as used herein refers to any number equal to or greater than 2. In some embodiments, the promoter may contain a modification in one or more regulatory protein (e.g., transcription factor) binding sites. In some embodi-ments, the promoter may contain one or more modifications in one or more regulatory protein (e.g., transcription factor) binding sites.

In some embodiments, a modified promoter having "reduced affinity" for a cognate regulatory protein may bind to the cognate regulatory protein with an affinity that is reduced by at least 5%, at least 10%, at least 20%, at least 30%, at least 40%, at least 50%, at least 60%, at least 70%, at least 80%, at least 90%, at least 99% relative to the binding affinity of the unmodified promoter to the same cognate regulatory protein, or any value and range therebe-tween. Each possibility represents a separate embodiment of the invention. In some embodiments, a modified promoter may bind to the cognate regulatory protein with an affinity that is reduced by 5-15%, 10-30%, 20-50%, 40-65%, 60-85%, 80-95%, or 90-99% relative to the binding affinity of the unmodified promoter to the same cognate regulatory protein. Each possibility represents a separate embodiment of the invention.

In some embodiments, a SMID system of the invention, is designed to detect or to generate a response to one or more input signals. In one embodiment, a SMID system may detect or generate a response to at least 2, at least 3, at least 4, at least 5, at least 6, at least 7, at least 8, at least 9, or at least 10 input signals, or any value and range therebetween. Each possibility represents a separate embodiment of the invention. In one embodiment, a SMID system may detect or generate a response to 2-4, 2-5, 3-6, 3-7, 2-8, 5-9, or 5-10 input signals. Each possibility represents a separate embodiment of the invention.

In some embodiment, a SMID system of the invention may express one or more output molecules. In one embodiment, a SMID system may express at least 2, at least 3, at least 4, at least 5, at least 6, at least 7, at least 8, at least 9, or at least 10 output molecules, or any value and range therebetween. Each possibility represents a separate embodiment of the invention. In one embodiment, a SMID system may express 2-4, 2-5, 3-6, 3-7, 2-8, 5-9, or 5-10 output molecules. Each possibility represents a separate embodiment of the invention.

Figure 1B:
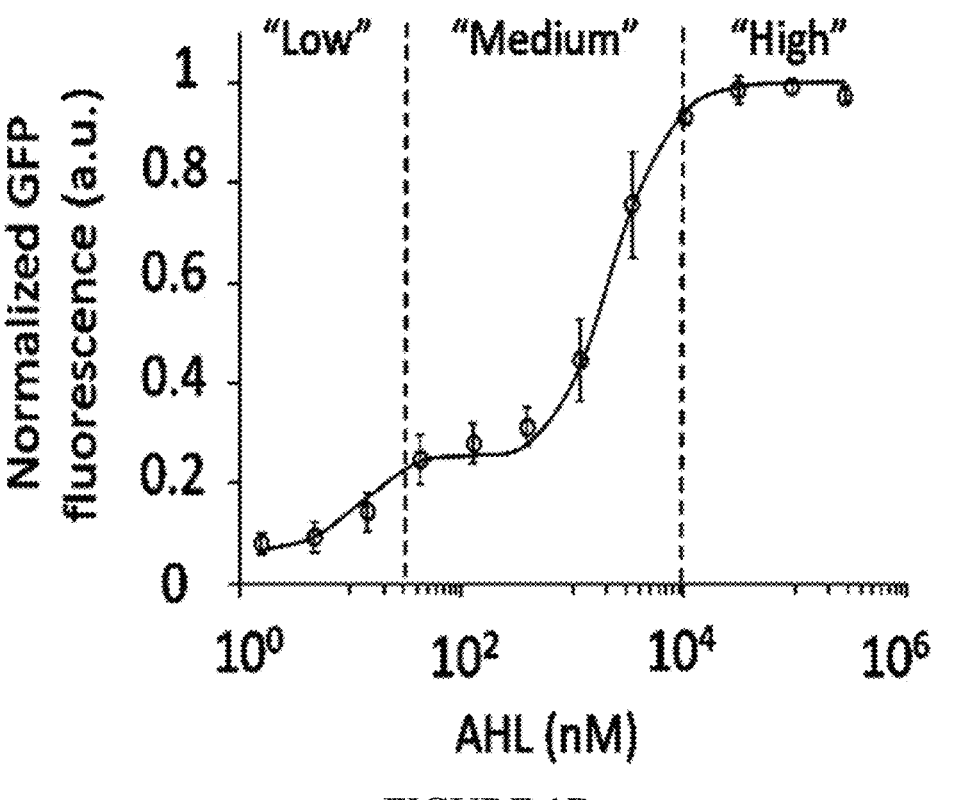

In some embodiments, a SMID system of the invention generates a response to a signal input, wherein the response is in the form of an output molecule. As used herein, the term "output molecule" refers to any detectable molecule or a detectable signal generated by the molecule, under the control of an input signal. Non-limiting examples of output molecules produced in response to activation of the plux promoter by AHL/LuxR are given herein in the form of the green fluorescent protein (GFP; FIGS. 1 and 2) or the red fluorescent protein—mCherry (FIG. 2). The expression level of an output protein, in some embodiments, depends on the affinity of a promoter for a particular regulatory protein. In one embodiment, the expression level of an output protein under the control of a modified promoter having reduced affinity for a regulatory protein is less than the expression level of the same output protein under the control of the unmodified promoter. In another embodiment, the expression level of an output protein under the control of a modified promoter having reduced affinity for a regulatory protein is less than the expression level of the same output protein under the control of a modified promoter having an even greater reduction in its affinity for the same regulatory protein.

In some embodiments, an output molecule comprises a polynucleotide. In some embodiments, the polynucleotide is encoding a peptide, polypeptide, or a protein. In some embodiments, the polynucleotide is a regulatory polynucleotide. In some embodiments, the polynucleotide is a catalytic polynucleotide. In some embodiments, the polynucleotide is an expression-interfering, translation-interfering polynucleotide, or both. In some embodiments, an output molecule comprises a protein. In some embodiments, an output molecule comprises a polynucleotide or a protein encoded therefrom.

As used herein, the terms "polynucleotide", "polynucleotide sequence", "nucleic acid sequence", and "nucleic acid molecule" are used interchangeably herein. The term "nucleic acid" is well known in the art. A "nucleic acid" as used herein will generally refer to a molecule (i.e., a strand) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C).

The terms "nucleic acid molecule" include but not limited to single-stranded RNA (ssRNA), double-stranded RNA (dsRNA), single-stranded DNA (ssDNA), double-stranded DNA (dsDNA), small RNA such as miRNA, siRNA and other short interfering nucleic acids, snoRNAs, snRNAs, tRNA, piRNA, tnRNA, small rRNA, hnRNA, circulating nucleic acids, fragments of genomic DNA or RNA, degraded nucleic acids, ribozymes, viral RNA or DNA, nucleic acids of infectious origin, amplification products, modified nucleic acids, plasmidial or organellar nucleic acids and artificial nucleic acids such as oligonucleotides. In some embodiments, the term "polynucleotide" comprises a vector or a plasmid comprising nucleobases.

As used herein, the terms "peptide", "polypeptide", and "protein" are used interchangeably to refer to a polymer of amino acid residues. In another embodiment, the terms "peptide", "polypeptide", and "protein" as used herein encompass native peptides, peptidomimetics (typically including non-peptide bonds or other synthetic modifications) and the peptide analogues peptoids and semipeptoids or any combination thereof. In another embodiment, the peptides polypeptides and proteins described have modifications rendering them more stable while in the body or more capable of penetrating into cells. In one embodiment, the terms "peptide", "polypeptide", and "protein" apply to naturally occurring amino acid polymers. In another embodiment, the terms "peptide", "polypeptide", and "protein" apply to amino acid polymers in which one or more amino acid residue is an artificial chemical analogue of a corresponding naturally occurring amino acid.

Non-limiting examples of output molecules include, but are not limited to, marker proteins such as fluorescent proteins (e.g., GFP, Enhanced (E)GFP, superfolder (sf)GFP, TagGFP, Turbo GFP, *Aequorea coerulescens* (Ac)GFP, Zoanthus sp. (Zs)GFP, Emerald, Azami green, mWasabi, T-Sapphire, Enhanced blue variant of GFP (EBFP), EBFP2, Azurite, mTagBFP, Enhanced cyan fluorescent protein (ECFP), mECFP, Cerulean, mTurquoise, CyPet, AmCyanl, Midori-ishi Cyan, TagCFP, mTFP1, Enhanced Yellow fluorescent protein (EYFP), Topaz, Venus, mCitrine, YPET, TagYFP, PhiYFP, ZsYellow1, mBanana, Kusabira Orange, Orange2, mOrange, mOrange2, dTomato, dTomato-Tandem, TagRFP, TagRFP-T, DsRed, DsRed2, DsRed-Express (T1), DsRed-Monomer, mTangerine, mRuby, mApple, mStrawberry, AsRed2, mRFP1, JRed, mCherry, HcRedl, mRaspberry, dKeima-Tandem, HcRed-Tandem, mPlum, AQ143 and variants thereof), enzymes (e.g., catalytic enzymes such as recombinases, integrases, caspases), biosynthetic enzymes, cytokines, antibodies, regulatory proteins such as transcription factors, polymerases and chromatin remodeling factors.

In some embodiments, the method further comprises a step of contacting the cell or cell lysate comprising the system of the invention with a suitable substrate molecule for an output molecule being an enzyme.

Non-limiting examples of output nucleic acid molecules include, but are not limited to, RNA interference molecules (e.g., siRNA, miRNA, shRNA), guide RNA (e.g., single-stranded guide RNA), trans-activating RNAs, riboswitches, ribozymes, and RNA splicing factors.

In some embodiments, the SMID system of the invention comprises one or multiple (e.g., 2, 3, 4 or more) copies of an output molecule. In some embodiments, the SMID system comprises two or more (e.g., 2, 3, 4 or more) different output molecules (e.g., 2 or more different fluorescent proteins such as GFP and mCherry, or two or more different types of output molecules such as a transcription factor or small RNAs that control transcription, and a fluorescent protein). In some embodiments, an output molecule is a regulatory protein which regulates expression of another output molecule (e.g., is a transcription factor that regulates a promoter, which drives expression of another output molecule).

In some embodiments, the SMID system of the invention, and components thereof, can be "tuned" or "modified". In some embodiments, the SMID system or components thereof are tuned or modified by promoter alteration. In some embodiments, promoter alteration refers to that the affinity of a positive-feedback promoter for a regulatory protein differs relative to the affinity of an output promoter for the same regulatory protein. In one embodiment, a SMID system further comprises a "regulatory sequence". In one embodiment, the regulatory sequence regulates transcription of an output molecule or regulatory protein. In one embodiment, the regulatory sequence regulates translation of an output molecule or regulatory protein. In one embodiment, the regulatory sequence regulates degradation of an output molecule or regulatory protein. In some embodiments, the regulatory sequence is a degradation tag. Non-limiting examples of a regulatory sequence include, but are not limited to, a ribosomal binding site (RBS), a riboswitch, a ribozyme, a guide RNA binding site, a microRNA binding site, a cis-repressing RNA, a siRNA binding site, and a protease target site. Regulatory sequences are typically located between a promoter and a nucleic acid to which it is operably linked such that the regulatory sequences is capable of regulating transcription and/or translation of the downstream (3') nucleic acid and/or output molecule. In some embodiments, a regulatory sequence is located in the 5' untranslated region (UTR) of a polynucleotide encoding an output molecule (e.g., gene or a transcript thereof). In some embodiments, a regulatory sequence is located in the 3' UTR of a nucleic acid and controls degradation of the nucleic acid. In some embodiments, a regulatory sequence is transnationally-fused to a protein-coding sequence so as to affect stability and/or intracellular-localization of the protein.

In some embodiments, the RBS is selected from: RBS30, RBS31, and RBS34.

In some embodiments, the ribozyme is RiboJ.

In some embodiments, the SMID system of the invention may further comprise other regulatory sequences. A non-limiting example of another type of a regulatory sequence comprises an aptamer, which can be evolved in vitro to bind any molecule and then used to control a riboswitch.

In some embodiments, a SMID system can be tuned such that a second input signal affects translation strength of an output molecule. For example, a riboswitch may be used to regulate translation of an output molecule.

As used herein, the term "riboswitch" refers to a compound comprising RNA, which senses its ligand in a preformed binding pocket and performs a conformational switch in response to ligand binding resulting in or leading to an altered gene expression. Non-limiting examples of riboswitches for use in a SMID system of the invention, include, but are not limited to, SAM/SAM-I, SAM/SAM-II, SAM/SAM-III, TPP, purine/G, purine/A, Purine/dG, lysine, Mg²⁺/ykoK, and/or others.

In some embodiments, tuning is achieved by modifying a ribosomal binding site located between a promoter and a nucleic acid to which it is operably linked. In one embodiment, modifying comprises mutating. In some embodiments, tuning comprises controlling the level of nucleic acid expression of particular components of the SMID system. In one embodiment, controlling comprises controlling copy number of the nucleic acids, such as by using one or more of a low, a medium, or a high copy plasmid, and/or constitutively-active promoters.

In some embodiments, combining two or more tuning mechanisms as provided hereinabove renders the SMID system of the invention "tunable". In some embodiments, the SMID system comprises a modified promoter (such as having reduced affinity for a regulatory protein) and a regulatory sequence (such as a riboswitch). In some embodiments, the SMID system comprises a modified promoter and a modified ribosomal binding site. In some embodiments, the SMID system comprises a modified ribosomal binding site and regulatory sequence.

In some embodiments, the promoters of the SMID system may be on the same polynucleotide (e.g., a vector or a plasmid) or on different polynucleotides (e.g., each on separate vectors or plasmids). In some embodiments, a vector is a low copy plasmid. In some embodiments, a vector is a medium copy plasmid. In some embodiments, a vector is a high copy plasmid. In some embodiments, SMID system of the invention comprises a low copy number plasmid, a medium copy number plasmid, a high copy number plasmid, or any combination thereof. Each possibility represents a separate embodiment of the invention.

The terms "vector" and "plasmid" are used herein interchangeably.

In some embodiments, promoters may be on the same vector. In some embodiments, the promoters may be on the same high copy vector, medium copy vector, or low copy vector, or any combination thereof. Each possibility represents a separate embodiment of the invention.

For clarity and ease of explanation, promoters responsive to a regulatory protein (or responsive to an input signal) may be referred to as first, second or third promoters (and so on) so as to distinguish one promoter from another. It should be understood that reference to a first promoter and a second promoter, unless otherwise indicated, is intended to encompass two different promoters (e.g., pLux, and pBAD). Similarly, output molecules may be referred to as a first, second or third output molecules (and so on) so as to distinguish one output molecule from another. It should be understood that reference to a first output molecule and a second output molecule, unless otherwise indicated, encompasses two different output molecules (e.g., GFP, and mCherry).

In some embodiments, promoters of the SMID system which are located on the same vector or plasmid may transcribe on the same direction or on opposite directions.

In some embodiments, the SMID system of the invention can be used to detect one or more input signals in a cell or a cell lysate. For example, the SMID system may comprise two components, one responsive to one input signal and another component responsive to another input signal, each component comprising a promoter (e.g., plux, and pBAD) responsive to a different regulatory protein and/or input signal (e.g., LuxR/AHL, and araC/arabinose) and operably linked to different output molecules (e.g., GFP, and mCherry). In some embodiments, the SMID system of the invention can generate independent responses to different input signals.

In some embodiments, mammalian expression vectors include, but are not limited to, pcDNA3, pcDNA3.1 (±), pGL3, pZeoSV2(±), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Stratagene, pTRES which is available from Clontech, and their derivatives.

In some embodiments, expression vectors containing regulatory elements from eukaryotic viruses such as retroviruses are used by the present invention. SV40 vectors include pSVT7 and pMT2. In some embodiments, vectors derived from bovine papilloma virus include pBV-1MTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

In one embodiment, plant expression vectors are used. In one embodiment, the expression of a polypeptide coding sequence is driven by a number of promoters. In some embodiments, viral promoters such as the 35S RNA and 19S RNA promoters of CaMV [Brisson et al., Nature 310:511-514 (1984)], or the coat protein promoter to TMV [Takamatsu et al., EMBO J. 6:307-311 (1987)] are used. In another embodiment, plant promoters are used such as, for example, the small subunit of RUBISCO [Coruzzi et al., EMBO J. 3:1671-1680 (1984); and Brogli et al., Science 224:838-843 (1984)] or heat shock promoters, e.g., soybean hsp17.5-E or hsp17.3-B [Gurley et al., Mol. Cell. Biol. 6:559-565 (1986)]. In one embodiment, constructs are introduced into plant cells using Ti plasmid, Ri plasmid, plant viral vectors, direct DNA transformation, microinjection, electroporation and other techniques well known to the skilled artisan. See, for example, Weissbach & Weissbach [Methods for Plant Molecular Biology, Academic Press, NY, Section VIII, pp 421-463 (1988)]. Other expression systems such as insects and mammalian host cell systems, which are well known in the art, can also be used by the present invention.

In some embodiments, in a 3 SMID system, the first promoter sequence and the sequence encoding a first regulatory protein, and the second promoter sequence and the sequence encoding a second regulatory protein, are located on separate expression vectors.

In some embodiments, in a 4 SMID system, the first promoter sequence and the sequence encoding a first regulatory protein, and the second promoter sequence and the sequence encoding a second regulatory protein, are located on separate expression vectors.

In some embodiments, in a 4 SMID system, the third promoter sequence and the sequence encoding a first output protein comprising a degradation tag and the fourth promoter sequence, and the fifth promoter sequence and the sequence encoding the first output protein, are located on separate expression vectors.

It will be appreciated that other than containing the necessary elements for the transcription and translation of the inserted coding sequence (encoding the polypeptide), the expression construct of the present invention can also include sequences engineered to optimize stability, production, purification, yield or activity of the expressed polypeptide.

Various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

In some embodiments, the SIMD system of the invention can be expressed in a broad range of host cell types. In some embodiments, SMID system is expressed in a bacterial cell, a yeast cell, a plant cell, an insect cell, a mammalian cell, or any other type of cell, or a lysate thereof. In some embodiments, the SMID system is expressed in a cell lysate. In some embodiments, the SMID system is expressed in an artificial cell system.

As used herein, the term "artificial cell" refers to any synthetically designed or engineered particle which is capable of simulating a function of a living cell. In some embodiments, an artificial cell comprises any one of: a nanoparticle, a liposome, a polymersome, a microcapsule, a vesicle, a cytostome, and the like. In some embodiments, the artificial cell is a fragment of a living cell. In some embodiments, the artificial cell originates or is derived from a living cell. In some embodiments, the artificial cell comprises synthetic compounds, such as synthetic polymers. In some embodiments, the artificial cell comprises both naturally occurring and synthetic compounds.

The terms "artificial cell", "minimal cell" are interchangeable.

Methods for obtaining a lysate from a cell are common and would be apparent to one of ordinary skill in the art.

As used herein, the term "artificial cell" refers to any engineered and/or synthetic particle having or capable of mimicking at least one function of a living cell.

In some embodiments, a bacterial cell is a Gram-negative cell. In some embodiments, the bacterial cell is a Gram-positive cell. Non-limiting examples of a bacterial cell include, *Yersinia* spp., *Escherichia* spp., *Klebsiella* spp., *Acinetobacter* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Salmonella* spp., *Vibrio* spp., *Bacillus* spp., *Erysipelothrix* spp., *Salmonella* spp., *Streptomyces* spp., *Bacteroides* spp., *Prevotella* spp., *Clostridium* spp., *Bifidobacterium* spp., or *Lactobacillus* spp. In some embodiments, the bacterial cell is *Bacteroides thetaiotaomicron*, *Bacteroides fragilis*, *Bacteroides distasonis*, *Bacteroides vulgatus*, *Clostridium leptum*, *Clostridium coccoides*, *Staphylococcus aureus*, *Bacillus subtilis*, *Clostridium butyricum*, *Brevibacterium lactofermentum*, *Streptococcus agalactiae*, *Lactococcus lactis*, *Leuconostoc lactis*, *Actinobacillus actinobycetemcomitans*, *cyanobacteria*, *Escherichia coli*, *Helicobacter pylori*, *Selnomonas ruminatium*, *Shigella sonnei*, *Zymomonas mobilis*, *Mycoplasma mycoides*, *Treponema denticola*, *Bacillus thuringiensis*, *Staphylococcus lugdunensis*, *Leuconostoc oenos*, *Corynebacterium xerosis*, *Lactobacillus plantarum*, *Lactobacillus rhamnosus*, *Lactobacillus casei*, *Lactobacillus acidophilus*, *Streptococcus* spp., *Enterococcus faecalis*, *Bacillus coagulans*, *Bacillus ceretus*, *Bacillus popillae*, *Synechocystis* strain PCC6803, *Bacillus liquefaciens*, *Pyrococcus abyssi*, *Selenomonas nominantium*, *Lac-*

*tobacillus hilgardii, Streptococcus ferus, Lactobacillus pentosus, Bacteroides fragilis, Staphylococcus epidermidis, Zymomonas mobilis, Streptomyces phaechromogenes,* or *Streptomyces ghanaenis.* As used herein, the term "endogenous bacterial cell" refers to a non-pathogenic bacteria which is a part of a normal internal ecosystem, such as the bacterial flora, or microbiome.

In some embodiments, the bacterial cell is an anaerobic bacterial cell (e.g., does not require oxygen for growth). In one embodiment, an anaerobic bacterial cell is a facultative anaerobic cell, and non-limiting examples of which include, *E. coli, Shewanella oneidensis* and *Listeria monocytogenes.* In another embodiment, an anaerobic bacterial cell is an obligate anaerobic cell, and non-limiting examples of which include, *Bacteroides* and *Clostridium* species.

In some embodiments, a SMID system as disclosed herein, is expressed in a mammalian cell. Non-limiting examples of a mammalian cell include, human cells, primate cells (e.g., vero cells), rat cells (e.g., GH3 cells, 0C23 cells), or mouse cells (e.g., MC3T3 cells). No-limiting examples of a human cell include, but are not limited to, human embryonic kidney (HEK) cells, HeLa cells, cancer cells from the National Cancer Institute's 60 cancer cell lines (NCI60), DU145 (prostate cancer) cells, Lncap (prostate cancer) cells, MCF-7 (breast cancer) cells, MDA-MB-438 (breast cancer) cells, PC3 (prostate cancer) cells, T47D (breast cancer) cells, THP-1 (acute myeloid leukemia) cells, U87 (glioblastoma) cells, SHSY5Y human neuroblastoma cells (cloned from a myeloma), and Saos-2 (bone cancer) cells. In some embodiments, engineered constructs are expressed in human embryonic kidney (HEK) cells (e.g., HEK 293 or HEK 293T cells). In some embodiments, the expression vectors disclosed herein, are expressed in stem cells (e.g., human stem cells) such as, for example, pluripotent stem cells (e.g., human pluripotent stem cells including human induced pluripotent stem cells (hiPSCs)).

The term "stem cell" refers to a cell with the ability to divide for indefinite periods in culture and to give rise to specialized cells. The term "pluripotent stem cell" refers to a type of stem cell that is capable of differentiating into all tissues of an organism, but not alone capable of sustaining full organismal development. The term "human induced pluripotent stem cell" refers to a somatic (e.g., mature or adult) cell that has been reprogrammed to an embryonic stem cell-like state by being forced to express genes and factors important for maintaining the defining properties of an embryonic stem cell. A human induced pluripotent stem cell expresses stem cell markers and is capable of generating cellular characteristic of all three germ layers (ectoderm, endoderm, mesoderm).

Additional non-limiting examples of cell lines that can be used to express the SMID system of the invention include 293-T, 293-T, 3T3, 4T1, 721, 9L, A-549, A172, A20, A253, A2780, A2780ADR, A2780cis, A431, ALC, B16, B35, BCP-1, BEAS-2B, bEnd.3, BHK-21, BR 293, BxPC3, C2C12, C3H-10T1/2, C6, C6/36, Cal-27, CGR8, CHO, CML T1, CMT, COR-L23, COR-L23/5010, COR-L23/CPR, COR-L23/R23, COS-7, COV-434, CT26, D17, DH82, DU145, DuCaP, E14Tg2a, EL4, EM2, EM3, EMT6/AR1, EMT6/AR10.0, FM3, H1299, H69, HB54, HB55, HCA2, Hepa1c1c7, High Five cells, HL-60, HMEC, HT-29, HUVEC, J558L cells, Jurkat, JY cells, K562 cells, KCL22, KG1, Ku812, KYO1, LNCap, Ma-Mel 1, 2, 3 . . . 48, MC-38, MCF-10A, MCF-7, MDA-MB-231, MDA-MB-435, MDA-MB-468, MDCK II, MG63, MONO-MAC 6, MOR/0.2R, MRCS, MTD-1A, MyEnd, NALM-1, NCI-H69/CPR, NCI-H69/LX10, NCI-H69/LX20, NCI-H69/

LX4, NIH-3T3, NW-145, OPCN/OPCT Peer, PNT-1A/PNT 2, PTK2, Raji, RBL cells, RenCa, RIN-5F, RMA/RMAS, S2, Saos-2 cells, Sf21, Sf9, SiHa, SKBR3, SKOV-3, T-47D, T2, T84, THP1, U373, U87, U937, VCaP, WM39, WT-49, X63, YAC-1 and YAR cells.

In some embodiments, a cell as used herein may be modified. As used herein, the term "modified cell" encompasses a cell comprising an exogenous nucleic acid or a synthetic nucleic acid (i.e., does not occur in nature, e.g., a SMID system of the present invention). In some embodiments, a modified cell contains a mutation in a genomic nucleic acid (e.g., compared to the wild type). In some embodiments, a modified cell contains an exogenous and/or independently replicating nucleic acid (e.g., components of the SMID system present, located, or integrated to an episomal vector). In some embodiments, a modified cell is produced by introducing an exogenous or synthetic nucleic acid into a cell.

Methods for introducing nucleic acid into cells are common and would be apparent to one of ordinary skill in the art. Non-limiting examples include, electroporation (see, e.g., Heiser W. C. Transcription Factor Protocols: Methods in Molecular Biology™ 2000; 130: 117-134), chemical (e.g., calcium phosphate or lipid) transfection (see, e.g., Lewis W. H., et al., Somatic Cell Genet. 1980 May; 6(3): 333-47; Chen C., et al., Mol Cell Biol. 1987 August; 7(8): 2745-2752), fusion with bacterial protoplasts containing recombinant plasmids (see, e.g., Schaffner W. Proc Natl Acad Sci USA. 1980 April; 77(4): 2163-7), transduction, conjugation, or microinjection of purified DNA directly into the nucleus of the cell (see, e.g., Capecchi M. R. Cell. 1980 November; 22(2 Pt 2): 479-88).

In some embodiments, a cell is modified according to the present invention so as to express or overexpress an endogenous protein of interest (e.g., via introducing or modifying a promoter or other regulatory element operably linked to the endogenous gene that encodes the protein of interest to so as to express the protein of interest or to increase its expression level). In some embodiments, a cell is modified by mutagenesis. In some embodiments, a cell is modified by introducing an engineered nucleic acid into the cell in order to produce a genetic change of interest (e.g., via insertion or homologous recombination). In some embodiments, the cell is modified by introducing a nucleic acid from a different organism, either from the same species or from a different specific. In some embodiments, a modified cell comprises a gene deletion.

In some embodiments, activation comprises specific activation. In some embodiments, specific activation denotes that a promoter is specifically activated only by being bound to a regulatory protein as described herein. In some embodiments, specific activation denotes that a protein is specifically expressed only by the promoter controlling the expression of a polynucleotide encoding the protein being bound to a regulatory protein as described herein.

In some embodiments, promoter as disclosed herein is activated for expression specifically by being contacted with an input signal as disclosed herein, e.g., AHL.

In some embodiments, promoter as disclosed herein is activated for expression specifically by being contacted with a regulatory protein as disclosed herein, e.g., Lux (such as LuxR), and AraC.

In some embodiments, a promoter as disclosed herein cannot or is not activated by any compound, e.g., a molecule, a regulatory protein, or others, other than the ones making the system of the invention. In some embodiments, a promoter as disclosed herein cannot or is not activated by a compound, e.g., a molecule, a regulatory protein, or others, being derived from a cell or a cell lysate comprising the system of the invention.

In some embodiments, components of the herein disclosed system specifically interplay with one another, e.g., activating the expression, regulating, degrading, and so forth, one another, but not comparable components, e.g., promoter, genes, peptides, of a cell or a cell lysate comprising the herein disclosed system.

In some embodiments, components of the herein disclosed system do not regulate cell endogenous promotors, endogenous protein expression, or both, of a cell or a cell lysate comprising the herein disclosed system.

In some embodiments, endogenous promoters, endogenous proteins, or both, of a cell or a cell lysate comprising the herein disclosed system, do not regulate, affect the expression, activity, or any combination thereof, the promoters, regulatory elements, regulatory proteins, output proteins, or other components of the herein disclosed system, or any combination thereof.

In some embodiments, the SMID system of the invention may be transiently expressed or stably expressed. The term "transient cell expression" refers to expression by a cell of a nucleic acid that is not integrated into the nuclear genome of the cell. For clarity, the term "stable cell expression" refers to expression by a cell of a nucleic acid that remains in the nuclear genome of the cell and its daughter cells. As used herein, the term "genome" refers to the nuclear genome, mitochondrial genome, chloroplast genome, plastid genome, or any combination thereof.

Methods of producing exogenous gene-stably expressing cells are well known in the art. Typically, to achieve stable cell expression, a cell is co-transfected with a marker gene and an exogenous nucleic acid (e.g., a SMID system or component thereof) that is intended for stable expression in the cell. The marker gene provides the cell with selectable advantage (e.g., resistance to a toxin, antibiotic, or other factors). Few transfected cells will, by chance, have integrated the exogenous nucleic acid into their genome. If a toxin, for example, is then added to the cell culture, only those few cells with a toxin-resistant marker gene integrated into their genome will be able to proliferate, while all other cells will die. After applying this selective pressure for a period of time, only the cells with a stable transfection remain and can be further cultured. Non-limiting examples of marker genes and selection agents include, dihydrofolate reductase with methotrexate, glutamine synthetase with methionine sulphoximine, hygromycin phosphotransferase with hygromycin, puromycin N-acetyltransferase with puromycin, and neomycin phosphotransferase with Geneticin, also known as G418. Other marker genes/selection agents are applicable and would be apparent to the skilled artisan.

Expression of nucleic acids in transiently-transfected and/or stably-transfected cells may be constitutive or inducible. Examples for inducible promoters are provided hereinabove.

In some embodiments, the system of the invention is sensor. In some embodiments, the system of the invention is a biosensor. In some embodiments, the system is used for diagnostics. In some embodiments, the system is used for environmental analysis. In some embodiments, the system is capable of detecting pollutants and/or toxins in a sample. In some embodiments, the sample is obtained or derived from a subject. In some embodiments, the sample is obtained or derived from the environment. In some embodiments, the sample is a water sample. In some embodiments, the sample comprises soil, water, or both, derived or obtained from the environment. In some embodiments, the system is used for determining hemorrhage in a subject.

Methods of Use

According to some embodiments, there is provided a method for expressing one or more output proteins using a single input signal, the method comprising: providing a cell or a cell lysate comprising the system of the invention; contacting the cell or the cell lysate with an input signal capable of activating the system; and detecting the expression of the one or more output proteins in the cell or the cell lysate.

Methods for detecting the expression of output or reporter genes are common and would be apparent to one of ordinary skill in the art. For example, in case the output molecule is a polynucleotide, such methods can include, but are not limited to, polymerase chain reaction (PCR; qPCR, qualitative PCR), northern-blot, RNA in-situ hybridization, and the like. In case the output molecule is a protein or a peptide, such methods can include, but are not limited to, fluorescent microscopy, confocal microscopy, ELISA (either fluorescent or enzymatic), MS-MS, and others.

According to some embodiments, there is provided a method for converting an analog signal to a digital output in a cell, the method comprising contacting the cell with a system as disclosed herein. In some embodiments, the cell comprises a system as disclosed herein. In some embodiments, the method comprises contacting the cell with an analog input signal. In some embodiments, the method comprises a step of determining a digital output in the cell, of the cell, or both.

In the description and claims of the present application, each of the verbs, "comprise", "include", and "have" and conjugates thereof, are used to indicate that the object or objects of the verb are not necessarily a complete listing of components, elements or parts of the subject or subjects of the verb.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

In the description and claims of the present application, each of the verbs, "comprise", "include", and "have" and conjugates thereof, are used to indicate that the object or objects of the verb are not necessarily a complete listing of components, elements or parts of the subject or subjects of the verb.

Other terms as used herein are meant to be defined by their well-known meanings in the art.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

EXAMPLES

Generally, the nomenclature used herein, and the laboratory procedures utilized in the present invention include molecular, biochemical, chemical and cell biology techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds.) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Strategies for Protein Purification and Characterization—A Laboratory Course Manual" CSHL Press (1996); all of which are incorporated by reference. Other general references are provided throughout this document.

Example 1

Three Single Input Multiplex Decision

The inventors designed a three-valued logic (ternary logic) using an AHL-GFP input-output transfer function (FIG. 1). Experimental results of the ternary data converter using the new design demonstrated that ternary logic can be achieved using neural networks. The data of ternary data converter was well fitted by the inventors' empirical models (see equations 1.1, and 1.2 below), with a set of model parameters:

MSB: $r_1 = 1.5$, $K_1 = 450$, $\beta_3 = 0.005$

LSB: $r_0 = 1.6$, $K_0 = 28$, $\beta_0 = 0.02$, $\alpha = 200$, $r_2 = 1.2$, $K_2 = 1$, $r_3 = 1.4$, $K_3 = 300$, $\beta_2 = 0.02$ Ternary genetic circuits, which convert analog signals to fuzzy levels, may find new applications in biotechnology such as allowing engineers to tune the expression level of toxic proteins, enzymes in metabolic pathways in a reliable way. In contrast to digital circuits which can report only in two states, ternary circuits such as disclosed herein can be used in constructing biosensors capable of reporting in three states: low, medium, or high.

$$MSB \propto \frac{\left(\frac{AHL}{K_1}\right)^{\tau_1} + \beta_1}{1 + \left(\frac{AHL}{K_1}\right)^{\tau_1}} \qquad \text{Eq. 1.1}$$

$$LSB \propto \frac{\left(\frac{AHL}{K_0}\right)^{\tau_0} + \beta_0}{1 + \left(\frac{AHL}{K_0}\right)^{\tau_0} + \alpha \cdot \left(\frac{MSB}{K_2}\right)^{\tau_2}} \cdot \left(\frac{1}{1 + \alpha \cdot \left(\frac{MSB}{K_3}\right)^{\tau_3}}\right) + \beta_2 \qquad \text{Eq. 1.2}$$

Example 2

Figure 2A:
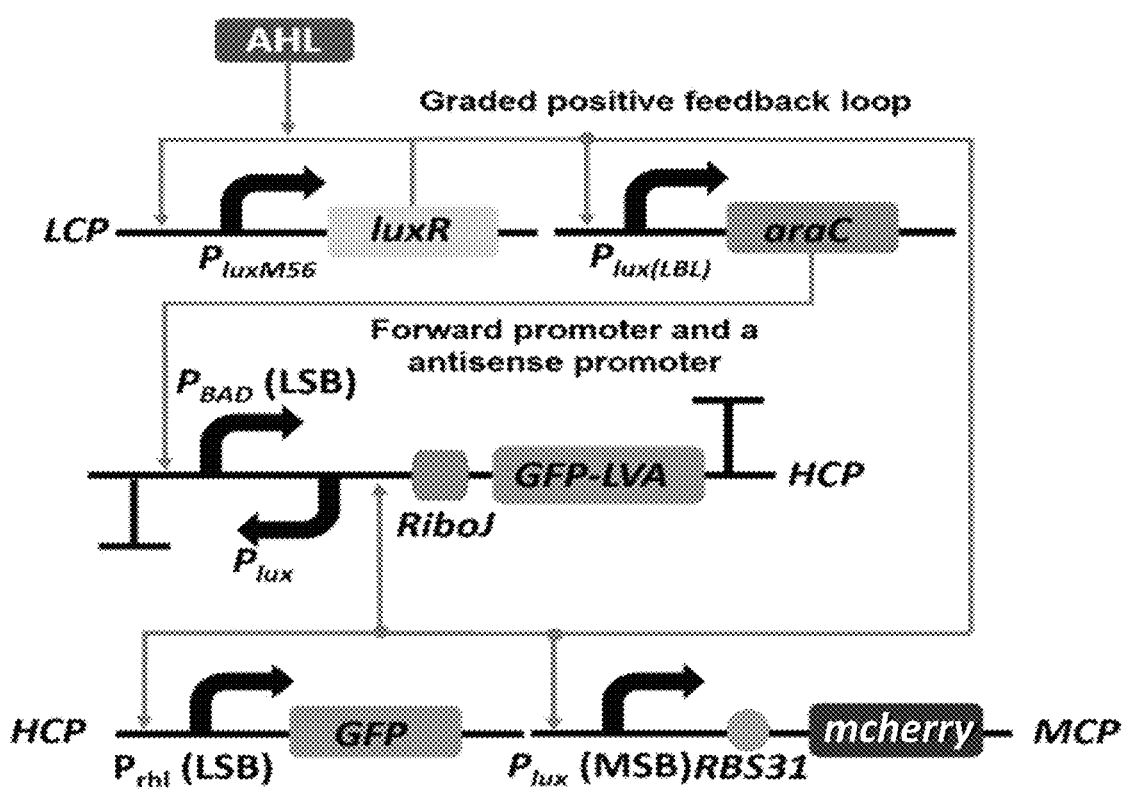
FIGS. 2A-2B are a non-limiting scheme of a four SMID system, and a graph showing how a single inducer or input signal (e.g., AHL) affects the expression of two reporter genes. A four states SIMD is implemented in *E. coli* bacteria cells using two transcription factors and two reporter genes. A non-limiting example of such reporter genes includes GFP and mCherry (which can be replaced by any other pair of different reporter genes). (2A) The four states SIMD comprises a mutated promoter, i.e., $P_{luxM56}$, providing a positive feedback loop, which regulates LuxR expression. The GFP signals are achieved from two parts of the system; (1) the forward $P_{BAD}$ promoter and antisense $P_{lux}$ promoter. The AraC is regulated by $P_{lux}$ (LBL) which is located on a LCP. The binding efficiency of RNA polymerase was altered to ensure low expression levels of AraC. The AraC and LuxR-AHL complex simultaneously bind to the forward $P_{BAD}$ and antisense $P_{lux}$ (promoter, respectively, which dynamically increase the threshold of $P_{BAD}$ switch and decrease the expression level of GFP; and (2) a $P_{rhl}$ promoter which is located on HCP, is activated by LuxR-AHL complex, and regulates the GFP signal for high AHL concentrations. To achieve comparable GFP signals from both parts of the system, an ssrA degradation tag (LVA) was added to the GFP under the regulation of the $P_{rhl}$ promoter. The $P_{lux}$ promoter, which is located on MCP, regulates the output of the mCherry protein. (2B) is a graph showing that GFP and mCherry can be expressed in a four states manner using the SMID system. Both mCherry and GFP are "off", (0,0); mCherry "off" GFP "on" (0,1); mCherry "on" GFP "off" (1,0); and both mCherry and GFP are "on", (1,1).
Figure 2B:
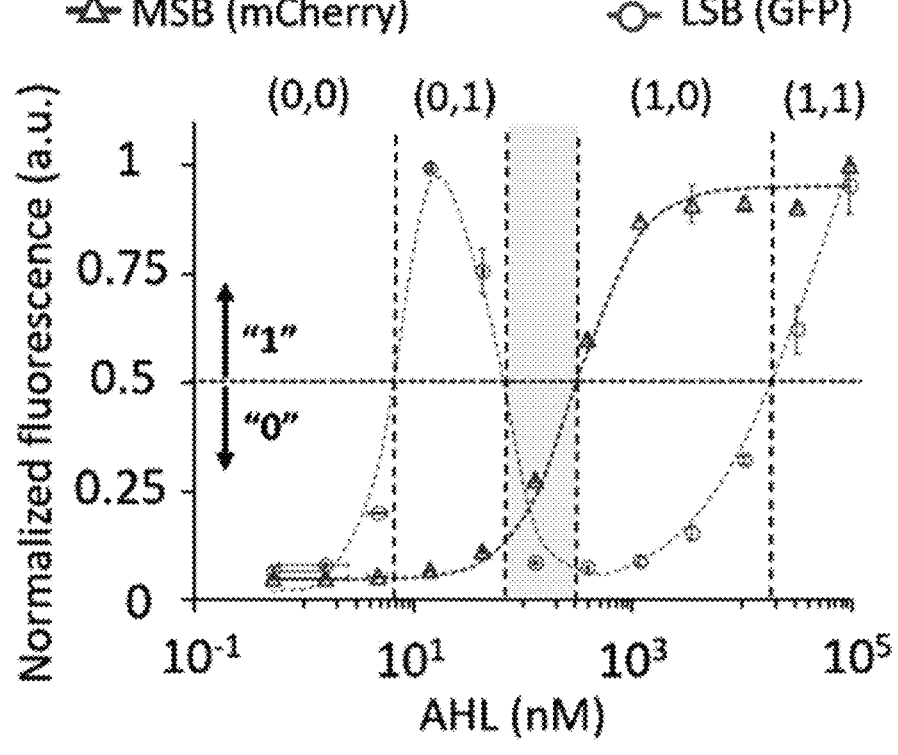

Four Single Input Multiplex Decision 2-bit Analog-to-Digital converter (ADC) which converts analog signals on a logarithmic scale to digital outputs, was constructed as shown in FIG. 2. The circuit receives AHL as an analog input and contains a graded positive feedback promoter ($P_{luxM56}$) which regulates LuxR. The LSB circuit was constructed from two GFP signals: (1) Forward $P_{BAD}$ promoter with antisense $P_{lux}$ promoter and (2) the $P_{rhl}$ promoter. The AraC regulated by P lux (LBL) is located on LCP (FIG. 2A). The inventors altered the binding efficiency of RNA polymerase to ensure a low expression level of AraC. The AraC and LuxR-AHL complex bind to the forward $P_{BAD}$ and antisense $P_{lux}$ promoter, respectively, which in turn increases the threshold of $P_{BAD}$ and decreases the expression level of GFP. The $P_{rhl}$ promoter located on HCP is activated by LuxR-AHL complex and regulates the GFP signal for high AHL concentrations. To achieve similar GFP levels in the two parts, an ssrA degradation tag (LVA) was added on HCP. The $P_{lux}$ of MSB circuit, which is located on MCP, regulates the output mCherry signal (FIG. 2A). Experimental results (FIG. 2B) showed that the 2-bit hybrid ADC had distinct four logic states (i.e., 4 SMID). The results further showed that 4 SMID has a narrow region in which the ADC has an irregular behavior (FIG. 2B).

TABLE 1

| List of parameters | |
|---|---|
| Symbol | Description |
| $\alpha$ | Fitting parameter |
| $\beta_i$ | Promoter basal level |
| $K_i$ | Effective dissociation constant |
| $r_i$ | Hill coefficients |

TABLE 2

List of abbreviations

| Symbol | Description |
| --- | --- |
| ADC | Analog to digital convertor |
| AHL | Free N-(β-Ketocaproyl)-L-homoserine Lactone 3OC$_6$HSL concentration |
| Arab | Free arabinose concentration |
| LSB | Last Significant Bit |
| LVA | ssrA degradation tag |
| MSB | Most Significant Bit |
| P$_{BAD}$ | AraC promoter is activated by the AracC when it is induced by arabinose (Arab) |
| P$_{lux}$ | LuxR promoter is activated by the LuxR when it is induced by AHL |
| P$_{luxMS6}$ | Mutated LuxR promoter is activated by the LuxR when it is induced by AHL |
| P$_{lux/tetO}$ | Combinatorial promoter |
| P$_{rhl}$ | Quorum sensing promoter that interacts with AHL inducer |
| TetR | Tet Repressor protein |

While certain features of the invention have been described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A system comprising:

a first expression vector comprising a first promoter sequence operably linked to a sequence encoding a first regulatory protein, wherein said first promoter is responsive to an input signal, and further comprising a second promoter sequence operably linked to a sequence encoding a second regulatory protein, wherein said second promoter is responsive to said first regulatory protein, and wherein said first expression vector is a low copy plasmid;

a second expression vector comprising a third promoter sequence operably linked to a sequence encoding a first output protein, wherein said third promoter is responsive to said second regulatory protein and wherein said sequence encoding said first output protein further comprises a degradation tag, and further comprising a first copy of a fourth promoter sequence located between said third promoter and said sequence encoding said first output protein, wherein said first copy of said fourth promoter sequence transcribes in a direction opposite to said third promoter sequence, and further comprising a fifth promoter sequence operably linked to a sequence encoding said first output protein, wherein said fifth promoter is responsive to said first regulatory protein, and wherein said second expression vector is a high copy plasmid; and a third expression vector comprising a second copy of said fourth promoter operably linked to a sequence encoding a second output protein, and wherein said third expression vector is a medium copy plasmid.

2. The system of claim 1, wherein: (i) said first promoter is responsive to said first regulatory protein; (ii) said second regulatory protein is expressed upon activation of said second promoter; and (iii) said first output protein of said second expression vector is expressed, upon activation of said fifth promoter.

3. The system of claim 2, wherein said first regulatory sequence is located between said third promoter and said sequence encoding said first output protein comprising a degradation tag of said second expression vector, and wherein said second regulatory sequence is located between said fourth promoter and said sequence encoding said second output protein of said third expression vector.

4. The system of claim 2, wherein any one of said first and said second regulatory sequences of said system is a non-coding polynucleotide.

5. The system of claim 4, wherein said non-coding polynucleotide is a catalytic polynucleotide.

6. The system of claim 5, wherein said catalytic polynucleotide is a ribozyme.

7. The system of claim 1, wherein (i) said first promoter sequence and said sequence encoding a first regulatory protein of said system, and said second promoter sequence and said sequence encoding a second regulatory protein of said system, are located on separate expression vectors; and (ii) wherein said third promoter sequence and said sequence encoding a first output protein comprising a degradation tag of said system, said fourth promoter sequence, and said fifth promoter sequence and said sequence encoding said first output protein of said system, are located on separate expression vectors.

8. The system of claim 1, wherein any one of: (i) said first promoter of said system is a mutated variant promoter of said system (a) or of any one of said first copy and said second copy of said fourth promoter of said system; (ii) wherein said first regulatory protein of said system binds to said mutated variant promoter of said system with reduced binding affinity compared to the binding affinity of said first regulatory protein to any one of said first copy and said second copy of said fourth promoter of said system; (iii) wherein said first promoter of said system is activated when bound to said input signal; (iv) wherein when said first promoter of said system is activated said first regulatory protein of said system is expressed; (v) wherein in said system said second promoter, said first copy and said second copy of said fourth promoter are activated when bound to said first regulatory protein; and (vi) wherein said third promoter said system is activated when bound to said second regulatory protein.

9. A cell or a cell lysate comprising the system of claim 1, optionally wherein said cell is a bacterial cell.

10. The cell or cell lysate of claim 9, further comprising an input signal.

11. A composition comprising the cell or cell lysate of claim 9.

12. A method for expressing one or more output proteins using a single input signal, the method comprising:

a. providing a cell or a cell lysate comprising said system of claim 1;

b. contacting said cell or said cell lysate with an input signal capable of activating said system; and c. detecting the expression of any one of said first and said second output proteins of said system in said cell or said cell lysate, optionally wherein said contacting comprises contacting said cell or said cell lysate with different concentrations of said input signal.

13. The method of claim 12, further comprising a step of determining the expression levels of any one of said first and said second output proteins.

14. A method for converting an analog signal to a digital output in a cell, the method comprising contacting said cell with the system of claim 1, thereby converting an analog signal to a digital output in the cell.

15. The system of claim 1, wherein said first regulatory protein binds to said fourth promoter with greater affinity than said first regulatory protein binds to said first promoter or said second promoter.

16. The system of claim 1, wherein when said fourth promoter is activated said second output protein is expressed, expression of said first output protein comprising a degradation tag from said second expression vector is repressed, or any combination thereof.

17. The system of claim 1, wherein when said third promoter is activated said first output protein comprising a degradation tag of said second expression vector is expressed.

18. The system of claim 1, wherein said second expression vector of further comprises a first regulatory sequence, and said third expression vector further comprises a second regulatory sequence.

19. The system of claim 18, wherein said first regulatory sequence is located between said fourth promoter and said sequence encoding said first output protein comprising a degradation tag of said second expression vector.

20. The system of claim 1, wherein said first regulatory sequence comprises a ribosomal binding site.

\* \* \* \* \*